United States Patent [19]
Edwards

[11] Patent Number: 4,629,456
[45] Date of Patent: Dec. 16, 1986

[54] TARGET RING FOR AN EYE DROPPER BOTTLE

[76] Inventor: David L. Edwards, 3844 S. Atlanta Pl., Tulsa, Okla. 74105

[21] Appl. No.: 303,421

[22] Filed: Sep. 18, 1981

[51] Int. Cl.⁴ .......................................... A61M 33/04
[52] U.S. Cl. ................................. 604/300; 604/294
[58] Field of Search .................... 128/233; 222/92; 604/300, 294, 295; 215/230, 341, 343, 346; 220/82 R; 221/64, 65

[56] References Cited

U.S. PATENT DOCUMENTS 2,736,316  2/1956  Stovall ................................ 604/300
3,446,209  5/1969  Macha ................................. 128/233

Primary Examiner—Thomas Wallen
Attorney, Agent, or Firm—William S. Dorman

[57] ABSTRACT

A target ring for a conventional eye dropper bottle having an upper conical nozzle received in a neck portion of the bottle and having an central orifice extending through the nozzle to be in communication with the interior of the bottle; comprising a contrasting target ring applied to a portion of the nozzle wherein the contrasting ring is outwardly concentric to the orifice thereby positioning the orifice in the center of the target.

4 Claims, 6 Drawing Figures

4,629,456

TARGET RING FOR AN EYE DROPPER BOTTLE

BACKGROUND OF THE INVENTION

1. Field of the Invention

The present invention relates to a simplified means to assist an individual in the self-application of medicated solutions to the eye. More particularly, the present invention relates to a contrasting ring or target applied to a portion of the surface of a medicinal eye dropper.

2. Prior Art

It is well known that the self-application of medicinal drops into the eye from a dispensing dropper bottle can be annoying. Many prescriptions of eye drops for prophylactic or therapeutic purposes are generally used by elderly persons. Current medications used in the control of glaucoma, for instance, have a dosage of one drop twice daily. These medicines are generally expensive so that it is essential, from an economic standpoint, that a drop be accurately placed in the eye and not wasted on the eyelid or face.

In a hospital the application of the eye drops is made by a nurse, since elderly persons may have lost some of their natural abilities and therefore have difficulty in applying the exact dosage to their own eye. Any unaided person will discover that as the eye dropper nozzle closely approaches the eye, the nozzle tip becomes fuzzy or out of focus, even for an individual who can keep his eye open and directed at the nozzle. Oftentimes people living alone, or those which have no one readily available to assist them in the proper application of the drops, may either forego the use of the drops or apply an excessive amount. Each of the above situations results in the recommended therapy of the doctor not being followed.

There are many devices in the prior art which attempt to solve the above problems inherent in the self-application of eye drops. Conventional eye cups use too much volume and are therefore wasteful of medication solutions which require only one or two drops a day. A prior art patent, U.S. Pat. No. 3,446,209 to Macha, discloses a device comprising an eye shield which resembles the lens portion of a pair of eye glasses. The nozzle portion of an eye dropper fits into an adaptor in the shield which itself is received in the eye glasses frame. Another patent, U.S. Pat. No. 3,945,381 to Silver, provides a cup-like member which surrounds the nozzle of the bottle and which is used to position the nozzle over the eye by surrounding the eyeball with the cup-like member. U.S. Pat. No. 4,111,200 to Sharra is similar to the Silver device except that a different cup arrangement is used.

No prior art discloses a means or a method to solve the above problems of self-application of eye drops without requiring an additional expense to the individual purchasing the medication. No prior art provides a means which is included as a component of the eye dropper bottle itself.

SUMMARY OF THE INVENTION

The present invention provides a means to facilitate in the self-application of medication solutions to the eye from a plastic squeeze-type dropper bottle. The present invention provides a target to direct the opening in the nozzle of an eye dropper bottle over the center of the eye and therefore eliminate waste of the medication solution. The present invention comprises a target ring applied to the upper portion of the surface of an eye dropper bottle so as to provide a necessary contrast with respect to the transparent or opaque surface of the bottle.

The target ring of the present invention is applied to various portions of the bottle surface to provide a visual target. The colored or contrasting ring is applied to either the base of the nozzle or to the nozzle tip which forms a smaller ring. Alternately, the entire nozzle could be colored or darkened thereby forming a larger and wider target ring. An individual focuses upon the center of the target, which is the opening in the bottle, to properly apply the medicinal eye drops.

DETAILED DESCRIPTION OF THE PREFERRED EMBODIMENTS

Figure 1:
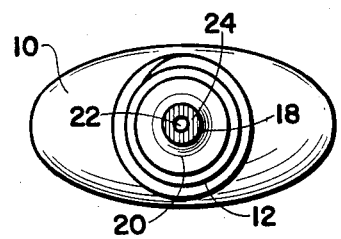
FIG. 1 is a top plan view of an eye dropper bottle showing a first target ring embodiment of the present invention.

Referring to FIGS. 1 to 4 in detail, the present invention is applied to a conventional eye dropper bottle 10 which is also referred to as a squeeze bottle. The bottle 10 is generally constructed from a plastic which can be either transparent or opaque. The bottle has an upper threaded portion or neck 12 which forms a mouth 14. The upper threaded portion 12 permits a screw-on cap (not shown) to be held in place.

The uppermost portion of bottle 10 is provided with a nozzle 16 having a central conical or cylindrical member 18 and a lower flat flange 20 which rests on top of the mouth 14. Nozzle 16 has an opening 22 in its flat tip 24 which opening extends through the nozzle to be in communication with the interior of the bottle 10 and the medication solution therein. To dispense drops through opening 24 the bottle is inverted and gently squeezed in a central area.

Figure 3:
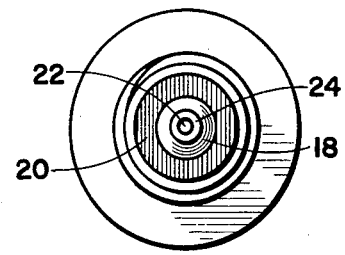
FIG. 3 is a top plan view showing a second target ring embodiment on a slightly different eye dropper bottle.
Figure 2:
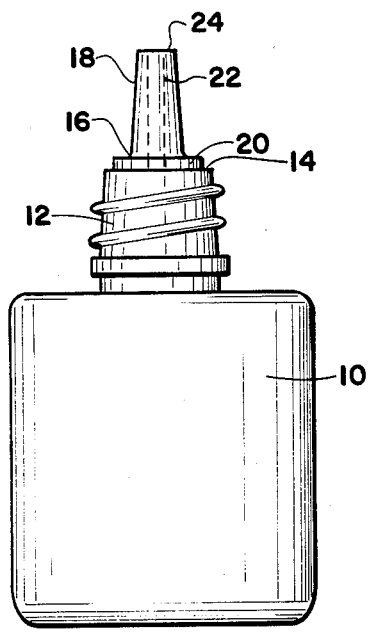
FIG. 2 is an elevational view of the eye dropper bottle in FIG. 1.
Figure 4:
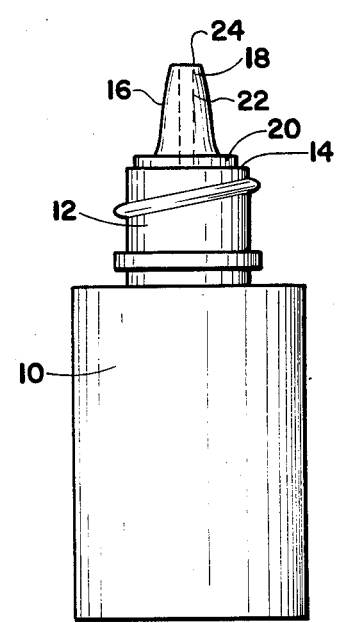
FIG. 4 is an elevational view of the eye dropper bottle in FIG. 3.
Figure 5:
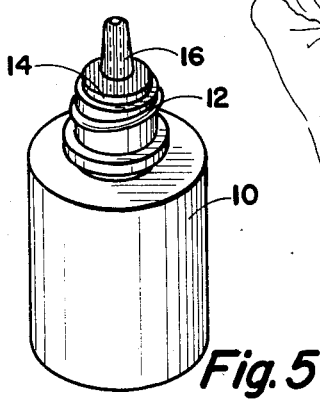
FIG. 5 is an elevational view of an eye dropper bottle showing a third target ring embodiment of the present invention.

In FIG. 1 a contrasting or colored ring of some type of non-toxic plastic pigment is applied to the tip 24 of the nozzle 16. A larger target ring is shown in FIG. 3 wherein the ring is applied to the flat upper surface of the lower flange 20. Generally, the nozzle is constructed so that it is a separate component having a bottom base (not shown) disposed beneath flange 20 and which is received within the interior of the mouth 14 of bottle 10. The nozzle 16 is readily removable from the bottle, therefore facilitating in the application of either of the two above described target rings to the eye dropper bottle. A third embodiment is shown in FIG. 5 wherein the target ring is formed by the entire outer surface of the nozzle; that is, the non-toxic pigmented coating is applied to the entire outer surface of the nozzle 16. The surrounding area of the mouth 14 will be, in effect, a white or colorless ring surrounding the nozzle.

A black plastic pigment is generally applied to the surface of the bottle 10 to form the above described contrasting rings or target. However, a color code system could be provided wherein a red ring would indicate drops which dilate the pupils, and a green ring would indicate drops which constrict the pupils of the eye, to correspond to current usage of these colors and to indicate the pharmaceutical effect by color of the cover top.

Figure 6:
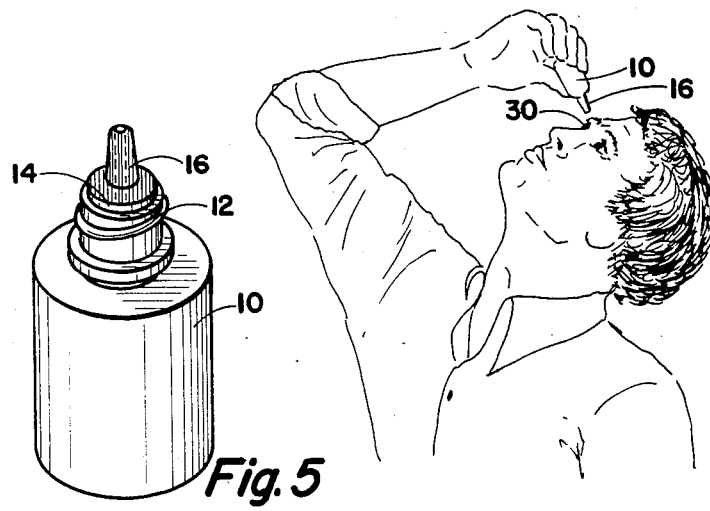
FIG. 6 is a perspective view of an individual employing the target ring of the present invention.

In order to properly apply medication from an eye dropper bottle 10 to the eye without waste, the orifice or opening 24 must be centered over the eye 30 of an individual as shown in FIG. 6. The targets described in FIGS. 1, 3 and 5 provide a means for the eye to focus upon the opening without the same becoming blurred. As shown, opening 24 is in the very center of each target, so that the opening can be readily disposed over the center of the eye which is the proper position for the drops to be dispensed. The only requirement upon the individual is to focus or "zero in" on the center of the target while simultaneously applying the proper dosage of medicated drops.

Whereas the present invention has been described in particular relation to the drawings attached hereto, it should be understood that other and further midifications, apart from those shown or suggested herein, may be made within the spirit and scope of this invention.

What is claimed is:

1. A target ring in combination with a conventional eye dropper bottle having an upper conical nozzle adjacent to a neck portion of said bottle and having a central orifice extending through said nozzle to be in communication with the interior of said bottle, and wherein said bottle is made from transparent or opaque material; comprising a target ring of contrasting color with respect to the color of the bottle, applied to at least a portion of said nozzle wherein said ring is outwardly concentric to said orifice thereby positioning said orifice in the center of said target ring.

2. A target ring as set forth in claim 1 wherein said contrasting ring is applied to the uppermost tip of said nozzle thereby forming a concentric ring directly adjacent said orifice.

3. A target ring as set forth in claim 1 wherein said contrasting ring is applied to a lower flat flange of said nozzle adjacent said neck of said bottle.

4. A target ring as set forth in claim 1 wherein said contrasting ring is applied to the entire outer surface of said nozzle surrounding said orifice.

* * * * *